United States Patent
Li et al.

(10) Patent No.: US 12,053,032 B2
(45) Date of Patent: Aug. 6, 2024

(54) METHOD ESTABLISHING FIRST AIRFLOW AND SECOND AIRFLOW IN E-VAPING CARTRIDGE

(71) Applicant: Altria Client Services LLC, Richmond, VA (US)

(72) Inventors: San Li, Midlothian, VA (US); Eric Hawes, Midlothian, VA (US); Raymond Lau, Richmond, VA (US); Robert Arents, Richmond, VA (US); Gerd Kobal, Sandy Hook, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 17/734,458

(22) Filed: May 2, 2022

(65) Prior Publication Data
US 2022/0264942 A1    Aug. 25, 2022

Related U.S. Application Data

(62) Division of application No. 16/679,815, filed on Nov. 11, 2019, now Pat. No. 11,317,651, which is a
(Continued)

(51) Int. Cl.
*A24F 40/10* (2020.01)
*A24F 7/00* (2006.01)
(Continued)

(52) U.S. Cl.
CPC ............... *A24F 7/00* (2013.01); *A24F 40/30* (2020.01); *A24F 40/485* (2020.01); *A61M 11/04* (2013.01);
(Continued)

(58) Field of Classification Search
CPC .......... A24F 40/10; A24F 40/20; A24F 40/30; A24F 40/485; A24F 7/00; A61M 11/003;
(Continued)

(56) References Cited

U.S. PATENT DOCUMENTS 6,694,975 B2   2/2004   Schuster et al.
6,701,922 B2   3/2004   Hindle et al.
(Continued)

FOREIGN PATENT DOCUMENTS

CN    102014677 A    4/2011
CN    102264249 A    11/2011
(Continued)

OTHER PUBLICATIONS

Russian Decision to Grant dated May 26, 2022, issued in corresponding Russian Patent Application No. 2020114234.
(Continued)

*Primary Examiner* — Abdullah A Riyami
*Assistant Examiner* — Thang H Nguyen
(74) *Attorney, Agent, or Firm* — Harness, Dickey & Pierce, P.L.C.

(57) ABSTRACT

The method including first establishing a first airflow in a first passage of an e-vaping cartridge, the first passage including a first portion, a second portion and a third portion, a first air inlet in communication with the first portion, a heater in communication with the second portion, the second portion being between the first portion and the third portion, and second establishing a second airflow in a second passage of the e-vaping cartridge, the second passage being in communication with the third portion.

18 Claims, 5 Drawing Sheets

Related U.S. Application Data division of application No. 15/712,353, filed on Sep. 22, 2017, now Pat. No. 10,506,830.

(51) Int. Cl.
| | | |
|---|---|---|
| *A24F 40/20* | (2020.01) | |
| *A24F 40/30* | (2020.01) | |
| *A24F 40/485* | (2020.01) | |
| *A61M 11/04* | (2006.01) | |
| *A61M 15/06* | (2006.01) | |
| *A61M 11/00* | (2006.01) | |
| *A61M 15/00* | (2006.01) | |
| *A61M 16/00* | (2006.01) | |

(52) U.S. Cl.
CPC .......... *A61M 11/042* (2014.02); *A61M 15/06* (2013.01); *A24F 40/10* (2020.01); *A24F 40/20* (2020.01); *A61M 11/003* (2014.02); *A61M 15/003* (2014.02); *A61M 15/002* (2014.02); *A61M 15/0021* (2014.02); *A61M 2016/0021* (2013.01); *A61M 2205/3334* (2013.01); *A61M 2205/8206* (2013.01); *A61M 2206/10* (2013.01)

(58) Field of Classification Search
CPC ................ A61M 11/04; A61M 11/042; A61M 15/0003; A61M 15/002; A61M 15/0021; A61M 15/06; A61M 2016/0021; A61M 2205/3334; A61M 2205/8206; A61M 2206/10

See application file for complete search history.

(56) References Cited

U.S. PATENT DOCUMENTS

| | | | |
|---|---|---|---|
| 7,802,569 B2 | 9/2010 | Yeates et al. | |
| 9,179,691 B2 | 11/2015 | Edwards et al. | |
| 9,282,772 B2 | 3/2016 | Tucker et al. | |
| 9,289,014 B2 | 3/2016 | Tucker et al. | |
| 9,986,760 B2* | 6/2018 | Macko | A24F 40/44 |
| 10,021,910 B2* | 7/2018 | Gavrielov | H05B 3/06 |
| 10,390,567 B2* | 8/2019 | Tucker | H05B 1/0244 |
| 2003/0051728 A1 | 3/2003 | Lloyd et al. | |
| 2008/0245363 A1 | 10/2008 | Korevaar et al. | |
| 2013/0233329 A1 | 9/2013 | Sebastian et al. | |
| 2013/0255702 A1 | 10/2013 | Griffith, Jr. et al. | |
| 2015/0196060 A1 | 7/2015 | Wensley et al. | |
| 2015/0208726 A1 | 7/2015 | Liu | |
| 2016/0021934 A1 | 1/2016 | Cadieux et al. | |
| 2016/0095357 A1 | 4/2016 | Burton | |
| 2016/0262456 A1 | 9/2016 | Borkovec et al. | |
| 2016/0262457 A1 | 9/2016 | Borkovec et al. | |
| 2016/0324216 A1* | 11/2016 | Li | A61M 15/002 |
| 2017/0135399 A1 | 5/2017 | Gavrielov et al. | |
| 2017/0245550 A1* | 8/2017 | Freelander | A61M 15/0051 |
| 2017/0258134 A1* | 9/2017 | Kane | H05B 3/56 |
| 2018/0020736 A1 | 1/2018 | Silvestrini et al. | |
| 2018/0042299 A1* | 2/2018 | Han | A24F 40/30 |
| 2018/0368478 A1* | 12/2018 | Golovanova | A24F 40/485 |
| 2019/0090538 A1* | 3/2019 | Li | A61M 15/06 |
| 2019/0246693 A1* | 8/2019 | Nettenstrom | F16J 15/10 |

FOREIGN PATENT DOCUMENTS

| | | |
|---|---|---|
| CN | 102679468 A | 9/2012 |
| CN | 104244749 A | 12/2014 |
| CN | 104783329 A | 7/2015 |
| CN | 105722417 A | 6/2016 |
| CN | 106998810 A | 8/2017 |
| CN | 108135290 A | 6/2018 |
| CN | 108697162 A | 10/2018 |
| EP | 3135136 A1 | 3/2017 |
| KR | 2004-0018585 | 3/2004 |
| RU | 2608915 C2 | 1/2017 |
| TW | 201330884 A | 8/2013 |
| TW | 201436722 A | 10/2014 |
| WO | WO-9748293 A1 | 12/1997 |
| WO | WO-2013/083635 A1 | 6/2013 |
| WO | WO-2016/179376 A1 | 11/2016 |
| WO | WO-2017/081299 A1 | 5/2017 |
| WO | WO-2017/093357 A1 | 6/2017 |

OTHER PUBLICATIONS

Office Action and Search Report dated Feb. 23, 2023 issued in corresponding Chinese Patent Application No. 201880056133.7.
International Search Report and Written Opinion issued Dec. 7, 2018 in corresponding PCT Application No. PCT/EP2018/075690.
International Preliminary Report on Patentability issued Aug. 28, 2019 in corresponding PCT Application No. PCT/EP2018/075690.
Office Action and Search Report dated Dec. 27, 2021, issued in corresponding Russian Patent Application No. 2020114234/03.
Office Action dated Oct. 17, 2022 issued in corresponding Japanese patent application No. 2020-516588.
Office Action dated Sep. 13, 2022, issued in corresponding Brazilian Patent Application No. 1120200037001.
Korean Office Action, dated Jun. 27, 2023, issued in Korean Patent Application No. 10-2020-7008223.
Chinese Notice of Allowance and Search Report dated Sep. 19, 2023, issued in corresponding Chinese Patent Application No. 201880056133.7.

* cited by examiner

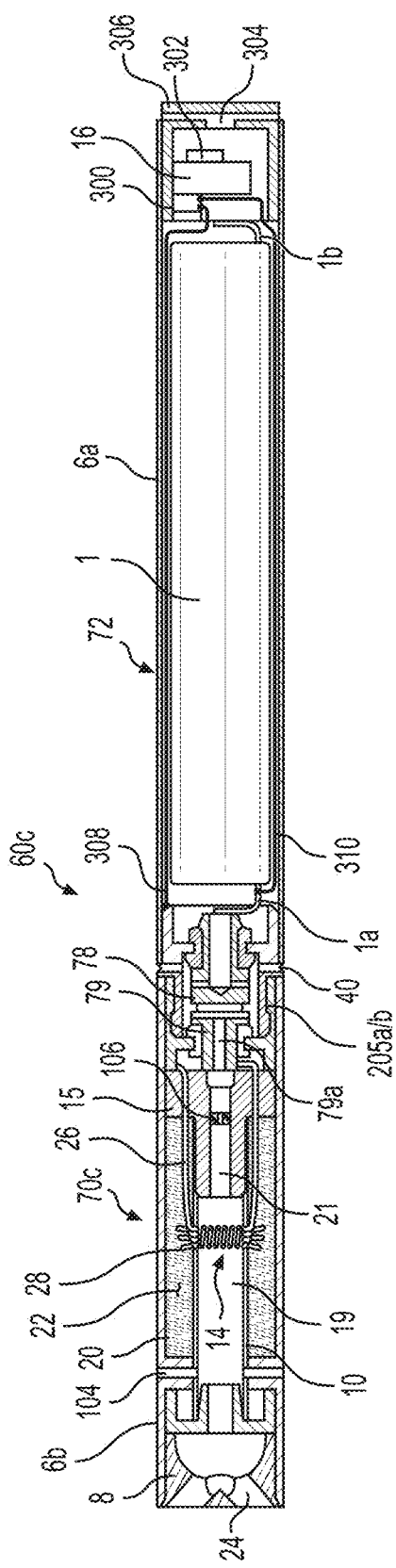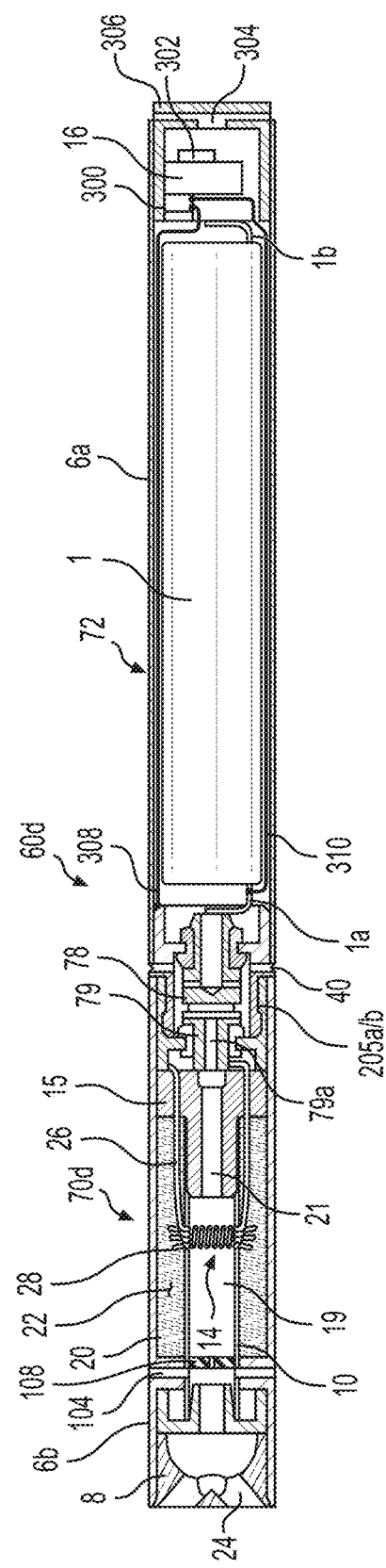
FIG. 4
FIG. 5

METHOD ESTABLISHING FIRST AIRFLOW AND SECOND AIRFLOW IN E-VAPING CARTRIDGE

CROSS-REFERENCE TO RELATED APPLICATION

This application is a divisional of U.S. application Ser. No. 16/679,815, filed on Nov. 11, 2019, which is a divisional of U.S. application Ser. No. 15/712,353, filed on Sep. 22, 2017, the entire contents of each of which are hereby incorporated by reference.

BACKGROUND

Field

Example embodiments relate generally to an air flow design for an electronic vaping (e-vaping) cartridge, including cartridges that include a non-combustible tobacco vaping insert, where the air flow design may benefit a sensory experience. Example embodiments also include a method of making the cartridge, and an e-vaping device that includes the cartridge.

Related Art

Electronic vaping (e-vaping devices, and in particular cartridges for an e-vaping device, may entrain an air-flow with an at least partially vaporized pre-vapor formulation in order to form a generated vapor within the device. The subsequently generated vapor may cool and condense, to some degree, as the generated vapor travels through the device prior to being discharged. As the vapor particles condense, the particles may coalesce and combine to form larger vapor particles, where a particle size distribution of the generated vapor may impact a sensory experience.

SUMMARY

At least one example embodiment relates to a cartridge.

In one embodiment, the cartridge includes a housing; a reservoir within the housing, the reservoir configured to contain a pre-vapor formulation; a first tube extending longitudinally within the housing, the first tube at least partially defining a central air passage, the central air passage including a first portion, a second portion and a third portion, the first portion, the second portion and the third portion of the central air passage being in communication with each other; a vapor generator in communication with the first portion of the central air passage, the vapor generator configured to communicate the pre-vapor formulation from the reservoir to the first portion of the central air passage and at least partially vaporize the pre-vapor formulation into a vapor; a first air inlet in communication with the second portion of the central air passage, the second portion of the central air passage being between the vapor generator and the first air inlet; and a dilution air inlet intersecting the third portion of the central air passage, the third portion of the central air passage being between the vapor generator and an outlet of the cartridge, the dilution air inlet defining a dilution air passage that does not pass through the vapor generator.

In one embodiment, the cartridge further includes an airflow restrictor within the central air passage, the airflow restrictor being positioned in at least one of the second portion of the central air passage and the third portion of the central air passage.

In one embodiment, the airflow restrictor is one of a flow tube and a gasket.

In one embodiment, the airflow restrictor is the flow tube, the flow tube having a length between about 8 mm and 12 mm, the flow tube having a first internal diameter between about 0.8 mm and 2 mm, and a second internal diameter of the first portion of the central air passage is in a range of about 2 mm to 6 mm.

In one embodiment, the airflow restrictor is the gasket, the gasket having a length of about 1 mm, the gasket having a third internal diameter between about 0.6 mm and 1.0 mm, and a fourth internal diameter of the first portion of the central air passage is in a range of about 2 mm to 6 mm.

In one embodiment, the airflow restrictor is in the third portion of the central air passage, wherein the dilution air inlet intersects the third portion of the central air passage between the outlet of the cartridge and a discharge end of the airflow restrictor.

In one embodiment, the airflow restrictor is in the second portion of the central air passage, wherein a discharge end of the airflow restrictor is spaced apart from the vapor generator by a distance of about 2 mm to 30 mm.

In one embodiment, the airflow restrictor is in the second portion of the central air passage, wherein a discharge end of the airflow restrictor is spaced apart from the vapor generator in order to cause an expected airflow through the cartridge to obtain an expected equilibrium Reynolds number prior to passing through the vapor generator during operational use of the cartridge.

In one embodiment, the housing defines a second air inlet for the cartridge, the second air inlet partially defining the dilution air passage.

In one embodiment, the central air passage and the dilution air passage are sized to provide a first expected volumetric airflow rate through the central air passage and a second expected volumetric airflow rate through the dilution air passage that is in a ratio of about 60:40 during operational use of the cartridge.

In one embodiment, an end of the dilution air inlet is in direct communication with the second portion of the central air passage, the dilution air inlet being a bypass vent that circumvents the vapor generator.

In one embodiment, the central air passage and the dilution air passage are sized to provide a first expected volumetric airflow rate through the central air passage and a second expected volumetric airflow rate through the dilution air passage that is in a ratio of about 1:1 during operational use of the cartridge.

In one embodiment, the cartridge further includes a non-combustible tobacco vaping insert positioned in at least one of the second portion and the third portion of the central air passage, wherein the vapor generator includes, a heater configured to at least partially vaporize the pre-vapor formulation, the heater being in communication with the first portion of the central air passage; and a wick in communication with the heater and the reservoir, the wick being configured to communicate the pre-vapor formulation from the reservoir to the heater.

At least another example embodiment relates to a method of making a cartridge.

In one embodiment, the cartridge includes a first tube extending longitudinally within a housing, the first tube at least partially defining a central air passage, the central air passage including a first portion, a second portion and a third portion of the central air passage that are in communication with each other, a vapor generator in communication with the first portion of the central air passage, and a first air inlet in communication with the second portion of the central air passage, the second portion of the central air passage being between the vapor generator and the first air inlet, where the method includes, providing a dilution air inlet in the cartridge, the dilution air inlet intersecting the third portion of the central air passage, the third portion of the central passage being between the vapor generator and an outlet of the cartridge, the dilution air inlet defining a dilution air passage that does not pass through the vapor generator; and inserting an airflow restrictor within the central air passage, the airflow restrictor being positioned in at least one of the second portion of the central air passage and the third portion of the central air passage, the airflow restrictor being one of a flow tube and a gasket.

In one embodiment, the flow tube has a length between about 8 mm and 12 mm and a first internal diameter between about 0.8 mm and 2 mm, the gasket has a length of about 1 mm and a second internal diameter between about 0.6 mm and 1.0 mm, and a third internal diameter of the first portion of the central air passage is in a range of about 2 mm to 6 mm.

In one embodiment, the housing defines a second air inlet for the cartridge, the second air inlet partially defining the dilution air passage.

In one embodiment, an end of the dilution air inlet is in direct communication with the second portion of the central air passage, the dilution air inlet being a bypass vent that circumvents the vapor generator.

At least another example embodiment relates to an e-vaping device.

In one embodiment, the e-vaping device includes, a cartridge including, a first housing, a reservoir within the first housing, the reservoir configured to contain a pre-vapor formulation, a first tube extending longitudinally within the first housing, the first tube at least partially defining a central air passage, the central air passage including a first portion, a second portion and a third portion of the central air passage that are in communication with each other, a vapor generator in communication with the first portion of the central air passage, the vapor generator configured to communicate the pre-vapor formulation from the reservoir to the first portion of the central air passage and at least partially vaporize the pre-vapor formulation into a vapor, a first air inlet in communication with the second portion of the central air passage, the second portion of the central air passage being between the vapor generator and the first air inlet, a dilution air inlet intersecting the third portion of the central air passage, the third portion of the central air passage being between the vapor generator and an outlet of the cartridge, the dilution air inlet defining a dilution air passage that does not pass through the vapor generator, an airflow restrictor within the central air passage, the airflow restrictor being positioned in at least one of the second portion of the central air passage and the third portion of the central air passage; and a power section connectable to the cartridge, the power section including, a second housing, the second housing defining a second air inlet, the second air inlet in communication with the first air inlet of the cartridge if the power section is connected to the cartridge, a sensor configured to sense an airflow through the central air passage if the power section is connected to the cartridge, and a power source configured to electrically energize the vapor generator of the cartridge if the power section is connected to the cartridge and the sensor senses an airflow through the central air passage.

In one embodiment, the airflow restrictor has a first cross-sectional area that is about 5% to 25% the size of a second cross-sectional area of the first portion of the central air passage, the airflow restrictor being one of a flow tube and a gasket, wherein the housing defines a third air inlet for the cartridge, the third air inlet partially defining the dilution air passage.

In one embodiment, the airflow restrictor has a first cross-sectional area that is about 5% to 25% the size of a second cross-sectional area of the first portion of the central air passage, the airflow restrictor being one of a flow tube and a gasket, wherein the dilution air inlet is in direct communication with the third portion of the central air passage, the dilution air inlet being a bypass vent that circumvents the vapor generator.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 4 illustrates an e-vaping device that includes a cartridge with a small diameter gasket and dilution air, in accordance with an example embodiment;

FIG. 5 illustrates an e-vaping device that includes a cartridge with a small diameter gasket and dilution air, in accordance with an example embodiment;

DETAILED DESCRIPTION

Figure 1:
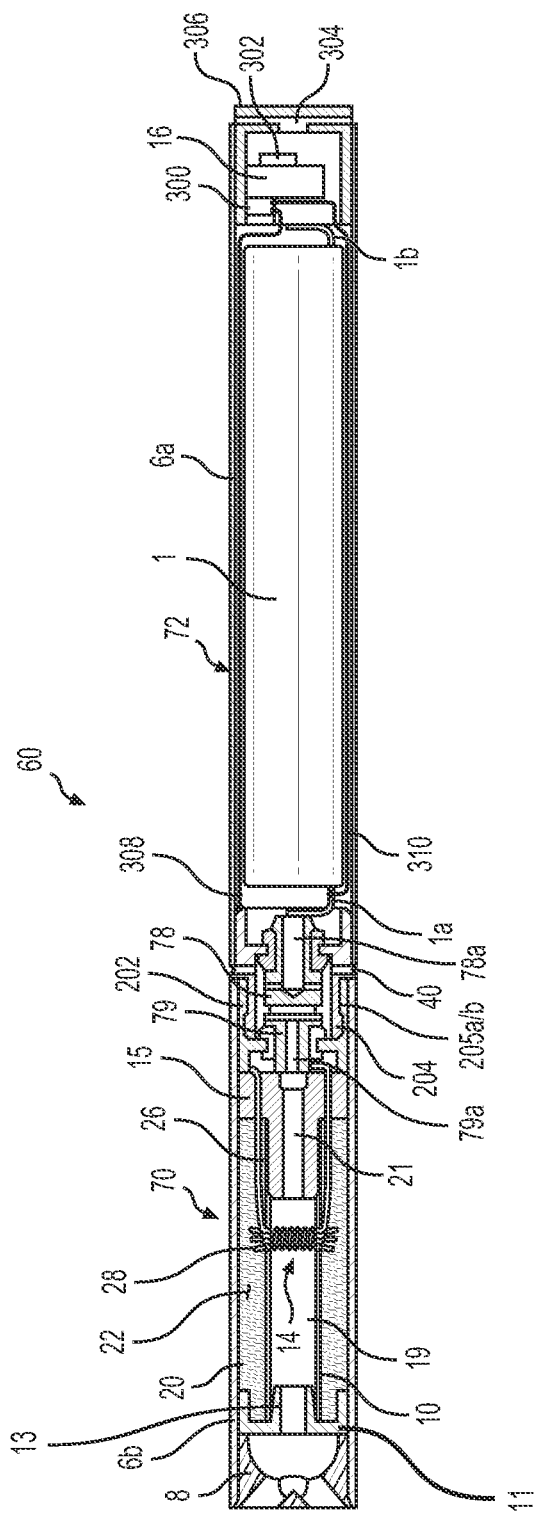
FIG. 1 illustrates an e-vaping device.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to" or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper" and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an" and "the" are intended to include the plural forms as well, unless the context clearly indicates otherwise. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 illustrates an electronic vaping (e-vaping) device 60. The device 60 may include two major sections: a cartridge 70, and a power section 72. The sections 70/72 may be connectable to each other, via a female connector 202 on the cartridge section 70 and a male connector 204 on the power section 72 (or, alternatively, the cartridge section 70 may have a male connector and the power section 72 may have a female connector). The sections 70/72 may be held together via mating threads 205a/b. Alternative to threads 205a/b, other structure may be used to connect the sections 70/72 to each other. For instance, friction fitting, snap fitting, adhesive, a removable and/or insertable pin, or other suitable structure may be used to join the sections 70/72 to each other. Optionally, the power section 72 may be permanently connected to the cartridge 70, such that the power section 72 may be an integral section of the cartridge 70.

The cartridge 70 may be a disposable section, or optionally the section 70 may instead be a non-disposable (rechargeable) section. The section 70 may include a "vapor generator," where the generator may include a vapor generating arrangement that may include a heater 14 surrounding a wick 28, where distal ends of the wick 28 may protrude into a reservoir 20 that make contain a pre-vapor formulation 22. The reservoir 20 may be at least partially defined by an inner tube 10 and a housing 6b of the cartridge 70. The heater 14 may be positioned within inner tube 10, where the wick 28 may draw the pre-vapor formulation 22 from the reservoir, via a capillary action, in order for the heater 14 to heat and vaporize the pre-vapor formulation 22.

In an embodiment, the wick 28 may be constructed of a fibrous and flexible material. The wick 28 may include at least one filament having a capacity to draw the pre-vapor formulation 22. For example, the wick 28 may include a bundle of filaments which may include glass (or ceramic) filaments. In another embodiment, a bundle may include a group of windings of glass filaments, for example, three of such windings, all which arrangements are capable of drawing pre-vapor formulation 22 via capillary action via interstitial spacing between the filaments.

In an embodiment, the heater 14 may be in the form of a wire coil, a planar body, a ceramic body, a single wire, a cage of resistive wire, or any other suitable form that may be configured to vaporize a pre-vapor formulation. The heater 14 may extend in a direction that may be transverse to a longitudinal length of the passage that the heater 14 may reside in (where the passage may be the outer air passage 19). In another embodiment, the heater 14 may be arranged to run along the longitudinal length of the outer air passage 19. The heater 14 may at least partially surround the wick 28. The heater 14 may extend fully or partially along a length of the wick 28, where the heater 14 may extend fully or partially around the circumference of the wick 28. In some example embodiments, the heater 14 may or may not be in contact with the wick 28.

In at least one example embodiment, the heater 14 may be formed of any suitable electrically resistive materials. Examples of suitable electrically resistive materials may include, but not limited to, copper, titanium, zirconium, tantalum and metals from the platinum group. Examples of suitable metal alloys may include, but not limited to, combinations of stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heater 14 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heater 14 may include at least one material selected from the group consisting of stainless steel, copper, copper alloys, nickel-chromium alloys, super alloys and combinations thereof. In an example embodiment, the heater 14 may be formed of nickel-chromium alloys or iron-chromium alloys. In another example embodiment, the heater 14 may be a ceramic heater having an electrically resistive layer on an outside surface thereof.

In another embodiment, the heater 14 may be constructed of an iron-aluminide (e.g., FeAl or $Fe_3Al$). Use of iron-aluminides can be advantageous in that they may exhibit high resistivity. FeAl may exhibit a resistivity of approximately 180 micro-ohms, whereas stainless steel may exhibit approximately 50 to 91 micro-ohms. The higher resistivity lowers current may draw or load on a power source 1 of section 72 of the device 60. Instead of using a wick 28, the heater 14 may be a porous material of sufficient capillarity and which may incorporate a resistance heater formed of a material having a high electrical resistance capable of generating heat quickly.

In other example embodiments, the heater 14 may be made of a sheet metal with two pieces bent into a semicircle and interlaced together. In other example embodiments, the heater 14 may be a serpentine heater placed inside the wick 28, a mesh heater, a flat plate heater, a Wismec Theorem heater with NotchCoil™, a spiral heater, a ceramic heating film, a curled heater and/or a platinum heater.

When activated, the heater 14 may be configured to heat a portion of the wick 28 surrounded by the heater 14 for less than about 10 seconds, or more preferably less than about 7 seconds. Thus, the power cycle may range in period from about 2 seconds to about 10 seconds (e.g., about 3 seconds to about 9 seconds, about 4 seconds to about 8 seconds, or about 5 seconds to about 7 seconds).

The mouth-end insert 8 of section 70 may either be permanently affixed on an end of the section 70, or alternatively mouth-end insert 8 may be removable. A seal 11 with a restricted air channel 13 (an example of a "second airflow restrictor," or a "pressure drop element") may be on an end of the inner tube 10. Another end of section 70 may be at least partially sealed by seal 15. Seal 15 may define a central air passage 21, where central passage 21 may be in fluid communication with an outer air passage 19 (where outer air passage 19 may be at least partially defined by inner tube 10), so that air may flow through central air passage 21, and then through outer air passage 19, when the section 70 is in operational use.

An anode terminal 79 may be affixed to an end of section 70, near the seal 15. The anode terminal 79 may at least partially held in place by connector 202. Electrical leads 26 may be attached to both ends of heater 14, in order to provide electrical power to the heater 14. Specifically, the electrical lead 26 may be electrically connected to connector 202 (where connector 202 may be electrically conductive), and electrical lead 26 be may be electrically connected to anode terminal 79.

In an embodiment, the pre-vapor formulation 22 may be a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol.

The pre-vapor formulation 22 may include volatile tobacco flavor compounds which may be released upon heating. The pre-vapor formulation 22 may also include tobacco elements dispersed throughout the formulation 22. When tobacco elements are dispersed in the pre-vapor formulation 22, the physical integrity of the tobacco element may be preserved. For example, the tobacco element may be 2-30% by weight within the pre-vapor formulation 22. Alternatively, the pre-vapor formulation 22 may be flavored with other flavors besides a tobacco flavor, or in addition to a tobacco flavor.

The reservoir 20 may be defined in an annulus space between the inner tube 10 and the housing 6b of the cartridge 70. The reservoir 20 may contain the pre-vapor formulation 22, and the reservoir 20 may optionally include a storage medium (not shown) configured to store the pre-vapor formulation 22 therein. The storage medium may include a winding of cotton gauze, a fibrous material, polyethylene, polyester, rayon and/or combinations thereof that may be wound around the inner tube 10.

Section 70 may be connectable to section 72 of the e-vaping device 60, where section 72 may be a power section that may include a power supply 1. The power section 72 may include a housing 6a that may contain a power supply 1, such as a battery. The battery may be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, power section 72 may be usable until the energy in the power supply 1 may be depleted. Alternatively, the power supply 1 may be rechargeable and reusable, and may include circuitry allowing the battery to be chargeable by an external charging device. In that case, the circuitry, when charged, may provide power for a desired (or alternatively, a determined) number of draws, after which the circuitry must be re-connected to an external charging device.

The power source 1 may have electrical connections 1a/b emanating from the power source 1. For instance, the power source 1 may have an anode connection 1a and a cathode connection 1b that may help create an electrical circuit to power the operations of the device 60. For instance, the power source 1 may be electrically connected to a sensor 16 and a control circuit 300 that may control an operation of the device 60. The control circuit 300 may be disposed on a rigid printed circuit board 302. The circuit board 302 may be connected to the first electrical connection 1*a* of the power supply 1 via electrical lead 308, and the circuit board 302 may be connected to the second electrical connection 1*b* via electrical lead 310. The power source 1 may also send an electrical current to the heater 14 of the cartridge 70 (as explained below in more detail).

Upon joining the sections 70/72 of the e-vaping device 60, air flow paths may exist in order to communicate an air flow between the sections 70/72. Specifically, an anode electrical post 78 of the power section 72 may define an air passage 78*a* through the post 78. The air passage 78*a* of post 78 may be in fluid communication with an air passage 79*a* that may be defined by anode terminal 79 of section 70 of the e-vaping device 60, where the air passages 79*a*/78*a* may allow the internal cavity of section 72 to be in fluid communication with the central air passage 20 of section 70. One or more air inlets 40 may be defined by connector 204 of section 72, where the air inlets 40 may also be in fluid communication with air passages 79*a*/78*a*. In an embodiment, the air inlets 40 may be positioned at several locations around a periphery of section 72.

In an assembled state, the e-vaping device 60 may form an electrical circuit that powers the operations of the device 60. The circuit may include the power source 1, the sensor 16, the control circuit 300, electrical leads 308/310, connectors 202/204 (where these connectors 202/204 may be made from an electrically conductive metal), the posts 78/79, the electrical leads 26, and the heater 14.

The E-Vaping Device in Operational Use:

Based on a structural understanding of the e-vaping device 60, as described above, an operation of the assembled device 60 is explained herein. Airflow through the device 60 may be caused by air being drawn into the cartridge 70 primarily from the air inlets 40, where the air may flow through the air passage 79*a* of the anode terminal 79, through the central air passage 20 and into the outer air passage 19. In outer air passage 19, the airflow may become entrained (eluted) by vapor that may be produced by the heater 14 heating the pre-vapor formulation 22 absorbed via the wick 28, prior to the airflow with the entrained vapor being discharged through an outlet 24 of the mouth-end insert 8.

Because the air passage 78*a* of post 78 may be in fluid communication with the air passage 79*a* of post 79, the sensor 16 may be capable of detecting vaping conditions (discussed below), so that the control circuit 300 may provide an electrical current from the power supply 1 to the heater 14 in order to heat and vaporize the pre-vapor formulation 22 that may be drawn to the heater 14 via the wick 28. In an embodiment, when activated, the heater 14 may heat a portion of the wick 28 for less than about 10 seconds.

The airflow through the device 60 may be used to activate the device 60. Specifically, the sensor 16 may be configured to generate an output indicative of a magnitude and direction of the airflow, where the control circuit 300 may receive the sensor 16 output and determine if the following vaping conditions exist: (1) a direction of the airflow indicates a draw on the mouth-end insert 8 (versus blowing air through the insert 8), and (2) a magnitude of the airflow exceeds a threshold value. If these internal vaping conditions of the device 60 are met, the control circuit 300 may electrically connect the power supply 1 to the heater 14, thereby activating the heater 14. Namely, the control circuit 300 may electrically connect the electrical lead 310 and electrical connection 1*b* (by activating a heater power control transistor forming part of the control circuit 300) so that the heater 14 may become electrically connected to the power supply 1. In an alternate embodiment, the sensor 16 may generate an output indicative of a pressure drop whereupon the control circuit 300 may activate the heater 14, in response thereto.

In an embodiment, the control circuit 300 may include a light 304, which the control circuit 300 may activate to glow when the heater 14 is activated and/or the power supply 1 is recharging. The light 304 may include one or more light-emitting diodes (LEDs). The LEDs may include one or more colors (e.g., white, yellow, red, green, blue, etc.). Moreover, the light 304 may be arranged to be visible to an adult tobacco consumer during vaping, where the light 304 may be positioned near the endcap 306 of the power section 72 of the e-vaping device 60. The light 304 may also be utilized for e-vaping system diagnostics. The light 304 may be configured such that an adult tobacco consumer may activate and/or deactivate the heater activation light 304 for privacy.

In an embodiment, the control circuit 300 may include a time-period limiter. In another embodiment, the control circuit 300 may include a manually operable switch for an adult tobacco consumer to initiate heating. The time-period of the electric current supply to the heater 14 may be set or pre-set depending on an amount of pre-vapor formulation 22 desired to be vaporized.

General Methodology:

Example embodiments may alter a vapor particle size distribution by adjusting an airflow design through an e-vaping device and/or an e-vaping cartridge. To that end, vapor particle growth by condensation and coagulation may be adjusted by altering a residence time of the vapor. In particular, the longer a vapor particle may be allowed to travel through the device, the more time the particle may have to coagulate while in contact with other vapor particles, in order to form larger particle drops. By introducing air ventilation (dilution air) downstream from a vapor generating region of the device, the residence time of particles formed in this region may be increased. Furthermore, structure used to create airflow restrictions (i.e., an "airflow restrictor"), either for airflow that is to travel through a vapor generating region, or for airflow leaving the vapor generating region, may also effectively increase the residence time of the particles in order to produce a larger average aggregate particle size for the vapor exiting the device. That is to say, the airflow for the device may be altered at a location that is either before or after the vapor generating region of the device.

The concept of increasing residence time for vapor particles that may condense and coalesce while traveling through an e-vaping device may also be applied to devices that include a non-combustible tobacco vaping insert 400/500 (shown in the embodiments of FIGS. 8 and 9, and described in more detail below), as the increased vapor particles may increase the effectiveness of the insert 400/500 in adding flavor to the generated vapor for the device.

Figure 2:
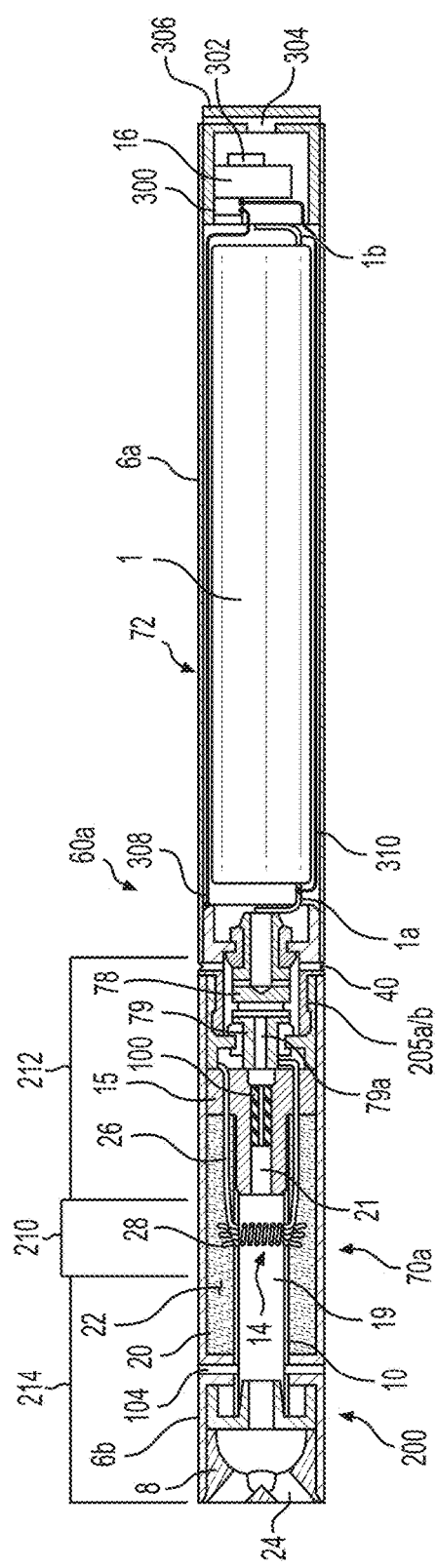
FIG. 2 illustrates an e-vaping device that includes a cartridge with a flow tube and dilution air, in accordance with an example embodiment.

FIG. 2 illustrates an e-vaping device 60*a* with a cartridge 70*a* that includes a flow tube 100 (an example of a "first airflow restrictor") and dilution air inlets 104, in accordance with an example embodiment. In an embodiment, the flow tube 100, which may be considered an "airflow restrictor," may be positioned at any point between the air inlets 40 and the heater 14, where a purpose of the flow tube 100 is to restrict (and therefore, slow) the flow of air traveling through the heater 14. To this end, for a cartridge 70*a* that is about 40 mm long, the outer air passage 19 (which houses the heater 14) may have an internal diameter in the range of 2 mm to 6 mm, or preferably 3 mm, where the flow tube 100 may be relatively long (as compared to the gaskets described in the following embodiments, below) with a length that may be between about 8 and 12 mm, and a preferred length that may be about 10 mm. In an embodiment, the length of the flow tube 100 may be about 20% to 30% of the length of the cartridge 70a, or most preferably about 25% of the length of the cartridge 70a. The flow tube 100 may have a central hole with an internal diameter (allowing air through the flow tube 100) that may be between about 0.8 mm and 2 mm, or preferably about 1 mm. In an embodiment, the flow tube 100 may have an internal diameter that may be about 10% to 40% the internal diameter of the outer air passage 19 that may house the heater 14, or more preferably about 15% to 35% the internal diameter of the outer passage 19, or most preferably about 33% of the internal diameter of the outer air passage 19. In the event the flow tube 100 includes a hole that is not circular, the hole may have a cross-sectional area that is about 0.005 mm$^2$ to 3.14 mm$^2$, or preferably about 0.785 mm$^2$ (corresponding to a 1.0 mm ID). In an embodiment, the flow tube 100 may have an internal diameter with a cross-sectional area that may be about 5% to 45% of the cross-sectional area of the internal diameter of the outer air passage 19 (the passage 19 that may house the heater 14), or more preferably about 5% to 30% of cross-sectional area of the internal diameter of the outer air passage 19, or most preferably about 10% of the cross-sectional area of the internal diameter of the outer air passage 19.

In an embodiment, the flow tube 100 may be fitted into the central passage 21 of the seal 15 of the cartridge 70a (as shown in FIG. 2). Or, alternatively, the flow tube 100 may be fitted, for instance, into the air passage 79a of the post 79 (where the air passage 79a may effectively be considered an "air inlet" for the cartridge 70a, in the event the air inlet 40 for the device 60a is located on the power section 72). Furthermore, the flow tube 100 may be fitted into the outer air passage 19 of the cartridge 70a, assuming a length of the outer air passage 19 is long enough to contain the flow tube 100. In particular, it should be understood that the flow tube 100 should be spaced apart from the heater 14, such that the tube 100 should not directly abut the heater 14. That is to say, the flow tube 100 should not be close enough to the heater 14 that the flow tube 100 may cause a thin stream of relatively high-velocity air to penetrate through the heater 14 (as air flowing through the flow tube 100 will have a relatively higher velocity, due to the small internal diameter of the tube 100), as doing so may be counter-productive to providing a relatively slower-velocity stream of air to pass by the heater 14. For this reason, the flow tube 100 may be spaced apart from the heater by at least about 2 to 30 millimeters, where this distance may ultimately be dependent on the expected velocity of air traveling through the cartridge 70a and the relative diameters of the tube 100 and the passage that the heater 14 is in (where, in FIG. 2, the heater 14 may be in the outer air passage 19, allowing for a further enhanced particle growth of vapor drops due to a cooling effect provided by this configuration). In an embodiment, the flow tube 100 may be spaced apart from the heater 14 by enough distance that an expected Reynolds number of the air passing through the heater 14 may approach an "expected equilibrium Reynolds number" that the air flow may continue to experience as the air approaches an end of the inner tube 10 (i.e., as the air approaches the location where the internal air flow through the cartridge 70a unites with dilution air from the dilution air inlets 104). That is to say, the flow tube 100 may be spaced apart from the heater 14 by enough distance that an expected air flow passing through heater 14 ideally will have fully developed (and, reached a stabilized Reynolds number value) to fill the outer air passage 19 as the air reaches the heater 14, in order to avoid a "thin blast of high-velocity air flow" that may otherwise occur at the heater 14, due to a restriction in the air flow that may be caused by the flow tube 100 (as a "thin blast of high-velocity air flow" may have a negative impact of vapor production at the heater 14).

A stream of dilution air may be provided at a location that is after the heater 14. That is to say, dilution air may be provided at any point between the heater 14 and the outlet 24 of the cartridge 70a (at the mouth-end insert 8). In an embodiment, dilution air may be provided via dilution air inlets 104 that may be in communication with the outer air passage 19 of the cartridge 70a, where the inlets 104 may be one or more in number. A size of the cross-sectional area of the dilution air inlets 104 may be dependent on some air flow parameters, where these "air flow parameters" may include: a size of the air inlets 40 of the device 60a, an expected volumetric air flow traveling through the cartridge 70a, the resistance to draw, a viscosity of the air and/or vapor flow, an internal diameter of the flow tube 100, and an average internal diameter of the entire air flow passage through the cartridge 70a (where the average internal diameter of the air flow passage through the cartridge 70a may include a diameter of the side vent 79b, the air passage 79a, the central passage 21 and the outer air passage 19, as an example). Each of these "air flow parameters," which may also include the cross-sectional area of the dilution air inlets 104, may influence an air velocity and/or a volumetric flowrate of air passing through the heater 14 (which, in turn, may govern a vapor particle size of vapor exiting the heater 14). These air flow parameters may also govern a divide between a volumetric flowrate of air passing by the heater 14, relative to a volumetric flowrate of air entering the dilution air inlets 104 (which, may in turn govern a vapor particle size of vapor exiting the heater 14). In an embodiment, a ratio of the volumetric flowrate of air though the cartridge to the volumetric flowrate of dilution air entering the dilution air inlets may be about 60 to about 40. In another embodiment, a cross-sectional area of the dilution air inlets 104 may be about 0.005 to 3.14 mm$^2$, and a cross-sectional area of the air inlets 40 for the device 60a may be about 3.14 to 0.005 mm$^2$.

In an example embodiment, a central airflow passage 200 is defined within the cartridge 70a. In an example embodiment, the central air passage 200 is defined by the following: the air inlets 40, the air passage 79a, the central passage 21, the outer air passage 19 and the outlet 24. That is to say, in an example embodiment, the central air passage 200 is a complete airflow path through the cartridge 70a. In an example embodiment, a first portion 210 of the central air passage 200 includes a portion of the outer air passage 19 that the heater 14 traverses. In an example embodiment, a second portion 212 of the central air passage 200 includes the air inlets 40, the air passage 79a, the central passage 21, a portion of the outer air passage 19 that is upstream of the heater 14. In an example embodiment, a third portion 214 of the central air passage 206 includes the outlet 24 and a portion of the outer air passage 19 that is downstream of the heater 14. This same description of the central airflow passage 200 applies to the other example embodiments shown in FIGS. 3-9.

Figure 3:
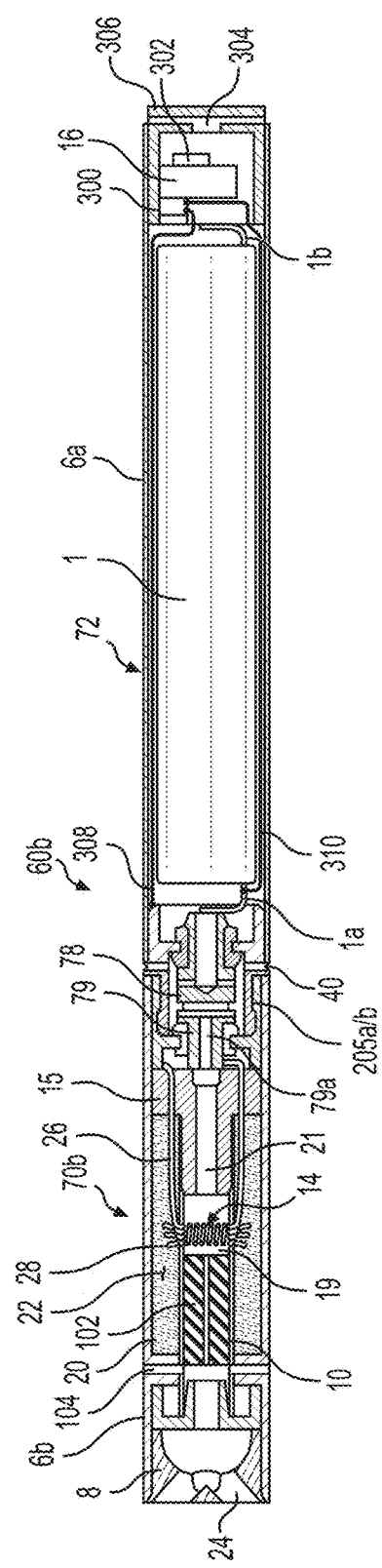
FIG. 3 illustrates an e-vaping device that includes a cartridge with a flow tube and dilution air, in accordance with an example embodiment.

FIG. 3 illustrates an e-vaping device 60b with a cartridge 70b that includes a flow tube 102 (an example of a "first airflow restrictor") and dilution air inlets 104, in accordance with an example embodiment. A general size of the cartridge 70b (i.e., overall length, and diameter of the outer air passage 19) may be a same size as the cartridge 70a, described above. In an embodiment, the flow tube 102, which may be considered another "airflow restrictor," may be positioned at any point between the heater 14 and the dilution air inlet (i.e., prior to the outlet 24 of the cartridge 70b at the mouth-end insert 8), where a purpose of the flow tube 102 is to significantly restrict (and therefore, slow) the air traveling through the heater 14. To this end, the tube 102 may have a same length and/or internal diameter as the tube 100 of FIG. 2.

Dilution air inlets 104 may be provided between an outlet of the flow tube 102 and an outlet 24 of the cartridge 70b, allowing dilution air to unite with air traveling through the heater 14 and the tube 102. In an embodiment, the dilution air inlets 104 may directly abut the discharge end of the flow tube 102. Physical characteristics of the dilution air inlets 104 (such as the cross-sectional area of the inlets 104) may be the same as the inlets 104 of the embodiment of FIG. 2 (as described above).

FIG. 4 illustrates an e-vaping device 60c that includes a cartridge 70c with a small diameter gasket (i.e., orifice plate) 106 and dilution air, in accordance with an example embodiment. A general size of the cartridge 70c (i.e., overall length, and diameter of the outer air passage 19) may be a same size as the cartridge 70a, described above. In an embodiment, the gasket 106, which may be considered an "airflow restrictor," may be positioned at any point between the air inlets 40 and the heater 14, where a purpose of the gasket 106 is to significantly restrict (and therefore, slow) the flow of air traveling through the heater 14. To this end, the gasket 106 may include a small-diameter hole with an internal diameter that may be about 0.6 mm to 1.0 mm, or preferably about 0.8 mm. In an embodiment, the internal diameter of the gasket 106 may be about 10% to 40% of the internal diameter of the outer air passage 19 that may house the heater 14, or more preferably about 15% to 35% of the internal diameter of the outer air passage 19, or most preferably about 25% of the diameter of the outer air passage 19. In the event the gasket 106 includes a hole that is not circular, the hole may have a cross-sectional area that is about 0.283 mm$^2$ to 0.785 mm$^2$, or preferably about 0.503 mm$^2$. In an embodiment, the internal cross-sectional area of the gasket 106 may be about 3% to 30% of the cross-sectional area of the outer air passage 19 that may house the heater 14, or more preferably about 5% to 25% of the cross-sectional area of the outer air passage 19, or more preferably be about 7% of the cross-sectional area of the outer air passage 19. The gasket 106 may have a relatively short length that may be, for instance, about 1 mm long. In an embodiment, the length (i.e., thickness) of the gasket 106 may be less than about 5% of the length of the cartridge 70c, or preferably about 2.5% of the length of the cartridge 70c. In another embodiment, the length of the gasket 106 may be negligible, relative to a length of the cartridge 70c.

In an embodiment, the gasket 106 may be fitted into the central passage 21 of the seal 15 of the cartridge 70c (as shown in FIG. 4). Or, alternatively, the gasket 106 may be fitted, for instance, into the air passage 79a of the post 79. Furthermore, the gasket 106 may be fitted into the outer air passage 19 of the cartridge 70c, assuming a length of the outer air passage 19 is long enough to contain the gasket 106. In particular, it should be understood that the gasket 106 should be spaced apart from the heater 14, using a same criteria as described above with regard to the flow tube 100 of the cartridge 70a described above (with regard to FIG. 2).

A stream of dilution air may be provided at a location that is between the heater 14 and an outlet 24 of the cartridge 70c. That is to say, dilution air may be provided at any point between the heater 14 and the outlet 24 of the cartridge 70c (at the mouth-end insert 8). In an embodiment, dilution air may be provided via dilution air inlets 104 that may be in communication with the outer air passage 19 of the cartridge 70c, where the inlets 104 may be one or more in number. Physical characteristics of the dilution air inlets 104 (such as the cross-sectional area of the inlets 104) may be the same as the inlets 104 of the embodiment of FIG. 2 (as described above).

FIG. 5 illustrates an e-vaping device 60d with a cartridge 70d that includes a small diameter gasket 108 and dilution air, in accordance with an example embodiment. A general size of the cartridge 70d (i.e., overall length, and diameter of the outer air passage 19) may be a same size as the cartridge 70a, described above. In an embodiment, the gasket 108, which may be considered an "airflow restrictor," may be positioned at any point between the heater 14 and a dilution air inlet 104 (i.e., prior to the outlet 24 of the cartridge 70d at the mouth-end insert 8). The gasket 108 may have a same length and/or internal pinhole diameter of the gasket 106 of FIG. 4 (described above). In an embodiment, the gasket 108 may be close enough to the heater 14 that the gasket 108 may directly abut the heater 14.

Dilution air inlets 104 may be provided between an outlet of the gasket 108 and an outlet 24 of the cartridge 70d, allowing dilution air to unite with air traveling through the heater 14 and gasket 108. In an embodiment, the dilution air inlets 104 may directly abut the discharge end of the gasket 108. Physical characteristics of the inlets 104 (such as the cross-sectional area of the inlets 104) may be the same as the inlets 104 of the embodiment of FIG. 2 (as described above).

Figure 6:
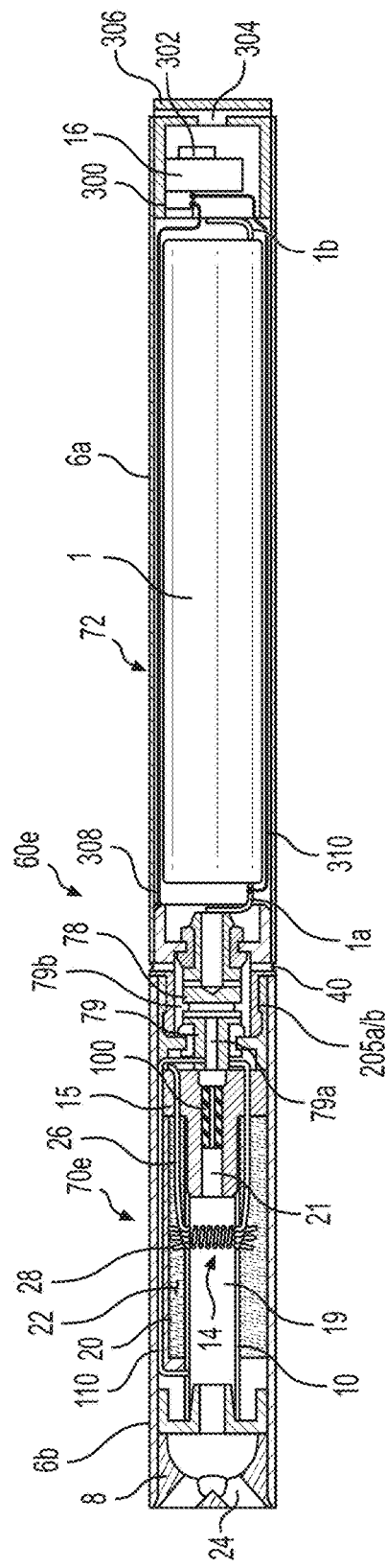
FIG. 6 illustrates an e-vaping device that includes a cartridge with a flow tube and air bypass, in accordance with an example embodiment.

FIG. 6 illustrates an e-vaping device 60e that includes a cartridge 70e with a flow tube 100 and air bypass, in accordance with an example embodiment. A general size of the cartridge 70e (i.e., overall length, and diameter of the outer air passage 19) may be a same size as the cartridge 70a, described above. Physical characteristics of the flow tube 100, such as a position of the tube 100 within the cartridge 70e, and an internal diameter of the tube 100, may be the same as that of flow tube 100 of FIG. 2 (described above).

The air bypass of the cartridge 70e may include a bypass vent 110 (where the bypass vent 110 may effectively be considered a "dilution air inlet"). The bypass vent 110 may include an inlet that may be connected to any location of the air flow channel between the air inlets 40 and the heater 14 (i.e., the inlet of the bypass vent 110 may therefore be connected, for instance, to the side vents 79b of the post 79, or the air passage 79a, or the central passage 21, and/or the outer air passage 19), thereby allowing the bypass vent 110 to circumvent the heater 14. An outlet of the bypass vent 110 may be connected to any location of the air flow channel between the heater 14 and the outlet 24 of the cartridge 70e (such as, for instance, the outer air passage 19 of the cartridge 70e).

The bypass vent 110 of the cartridge 70e may be sized based on at least some of the following "bypass flow parameters": a size and/or cross-sectional area of the air inlets 40 of the device 60e, an expected volumetric air flow traveling through the cartridge 70e, a viscosity of the air and/or vapor flow, an internal diameter of the flow tube 100, an average internal diameter of the entire air flow passage through the cartridge 70e (where the average internal diameter of the air flow passage through the cartridge 70e may include a diameter of the side vents 79b, the air passage 79a, the central passage 21 and the outer air passage 19, as an example), and a size and/or cross-sectional area of the bypass vent 110. In an embodiment, more than one bypass vent 110 may be included in the cartridge 70e. Each of these "bypass flow parameters" may influence an air velocity and/or a volumetric flowrate of air passing through the heater 14 (which, in turn, may govern a vapor particle size of vapor exiting the heater 14). These bypass flow parameters may also govern a divide between a volumetric flowrate of air passing by the heater 14, relative to a volumetric flowrate of air traveling through the bypass vent 110 (which, may in turn govern a vapor particle size of vapor exiting the heater 14). In an embodiment, a ratio of the volumetric flowrate of air though the heater 14 to the volumetric flowrate of bypass air traveling through bypass vent 110 may be about 1:1. In another embodiment, a cross-sectional area of the bypass vent 110 may be about 0.005 to 0.785 $mm^2$, and a cross-sectional area of the air inlets 40 for the device 60a may be about 0.283 to 0.785 $mm^2$.

Figure 7:
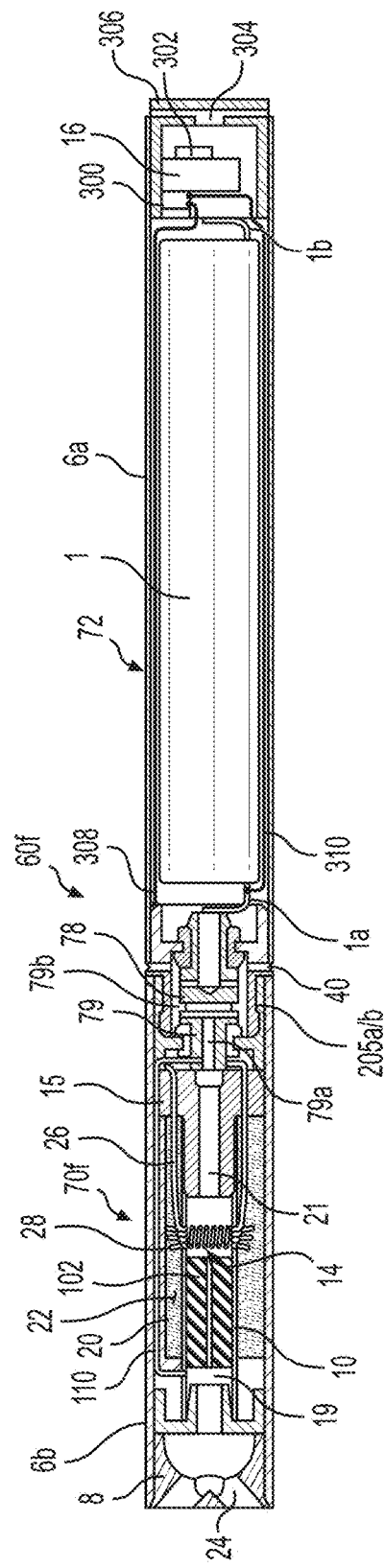
FIG. 7 illustrates an e-vaping device that includes a cartridge with a flow tube and air bypass, in accordance with an example embodiment.

FIG. 7 illustrates an e-vaping device 60f that includes a cartridge 70f with a flow tube 102 and air bypass, in accordance with an example embodiment. A general size of the cartridge 70f (i.e., overall length, and diameter of the outer air passage 19) may be a same size as the cartridge 70a, described above. In an embodiment, the flow tube 102 may be positioned at any point between the heater 14 and an outlet of the bypass vent 110. The flow tube 102 may have a same length and/or an internal diameter as the flow tube 102 of FIG. 3 (described above). In an embodiment, the flow tube 102 may be close enough to the heater 14 that the flow tube 102 may directly abut the heater 14.

The air bypass of the cartridge 70f may include a bypass vent 110. The bypass vent 110 may have physical characteristics (a location, and/or internal diameter) that may be determined on a same basis as the bypass vent 110 of the cartridge 70e of FIG. 6. In an embodiment, a size and/or cross-sectional area of the bypass vent 110 may be determined based on the same "bypass flow parameters" (as described above) as the bypass vent 110 of the cartridge 70e of FIG. 6.

Figure 8:
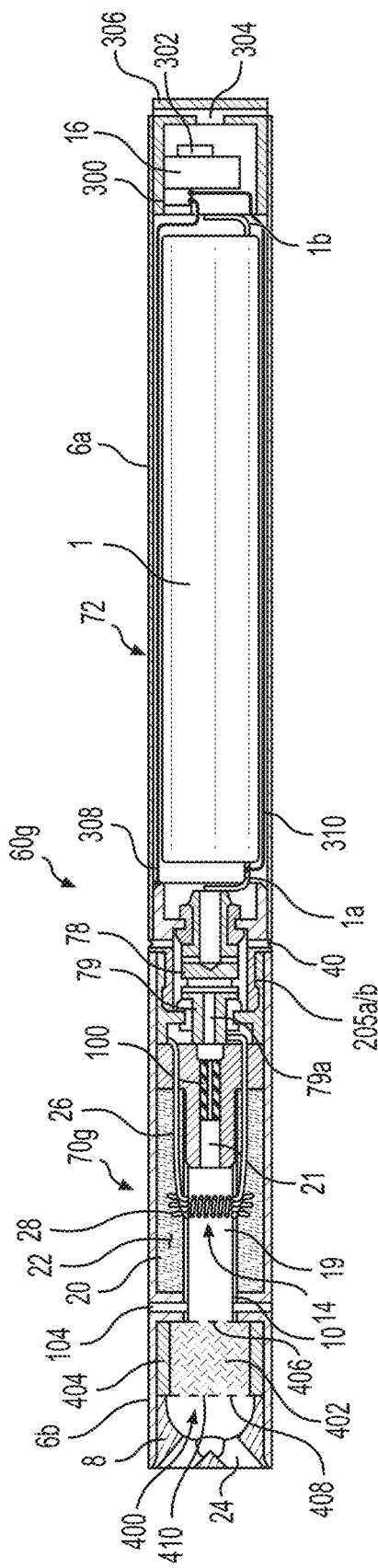
FIG. 8 illustrates an e-vaping device that includes a cartridge with a flow tube and dilution air, with a non-combustible tobacco vaping insert, in accordance with an example embodiment.

FIG. 8 illustrates an e-vaping device 60g that includes a cartridge 70g with a flow tube 100 and dilution air, with a non-combustible tobacco vaping insert 400, in accordance with an example embodiment. A general size of the cartridge 70g (i.e., overall length, and diameter of the outer air passage 19) may be a same size as the cartridge 70a, described above. The dilution air may be provided by one or more dilution air inlets 104. The location and physical characteristics (i.e., internal diameter) of the flow tube 100, and the physical characteristics and location of the dilution air inlets 104, is the same as the cartridge 70a of FIG. 2, and for brevity sake this information is therefore not repeated again, here.

An insert 400 may be fitted on an end of the cartridge 70g, at any location between the heater 14 and the outlet 24 of the cartridge 70g. By virtue of the existence of the insert 400 within the device 60g, the device may be considered a tobacco vapor system, as the device 60g may include both a tobacco system (including insert 400) and a vapor system (including the "vapor generating arrangement," where the heater 14 and wick 28 may be a part of this arrangement). Therefore, in an embodiment, the insert 400 may be positioned between the dilution air inlets 104 and the outlet 24 of the cartridge 70g, in order to have both the dilution air and the warm vapor (generated from heater 14) flow through the insert 400. In another embodiment, the dilution air inlets 104 may be positioned between the insert 400 and the outlet 24 of the cartridge 70g, such that only the warm vapor (generated from heater 14) may flow through the insert 400.

The insert 400 may include a cylindrical housing 404 that may be pressure-fitted within an end of the cartridge 70g, near a discharge of the outer air passage 19. Alternative to being pressure-fitted within the end of the cartridge 70g, the insert 400 may instead be held within the cartridge 70g via an adhesive, set screws, a snap-fit connecting structure, or any other structure necessary to hold the housing 404 of the insert 400 within a channel of the cartridge 70g. The insert 400 may either be permanently affixed within the cartridge 70g, or alternatively insert 400 may be temporarily held within the cartridge 70g, such that insert 400 may be removed and then replaced prior to the useful end-life of the cartridge 400 (where the insert 400 may be removed from the cartridge 70g via the mouth-end insert 8 first being removed from an end of the cartridge 70g, as an example). The housing 404 of the insert 400 may be a cylindrical housing made of aluminum, for example. The cylindrical housing 404 may have an outer diameter that fits, for instance, with an internal surface of the housing 6b (as shown in FIG. 8), or alternatively the housing 404 may be fitted within inner tube 10 (as another example embodiment). It should also be understood that more than one insert 400 may be included in the cartridge 70g.

The insert 400 may include a tobacco element 402 (an example of a "pressure drop element"). The term "tobacco element" may refer to any tobacco plant material including tobacco leaf, tobacco plug (compressed form of tobacco), tobacco strands, rolled tobacco, reconstituted tobacco, filler, tobacco beads, compressed tobacco rod, shaped tobacco, and/or powder tobacco, for example. The tobacco element 402 may be wrapped in natural tobacco, reconstituted sheet tobacco or aluminum, for example. In an alternative embodiment, flavor elements may be substituted for "tobacco elements" (as described herein), where "tobacco elements" may be one type of a "flavor element." The term "flavor element" may also include non-combustible flavor beads, flavor elements, or flavored-tobacco elements, where the flavoring may be something other than a tobacco flavoring, or the flavoring may include another flavoring in addition to a tobacco flavoring. While only one tobacco element 402 is illustrated in FIG. 8, it should be understood that a plurality of tobacco elements 402 may be used. Fibrous segments (e.g., cellulose acetate, other synthetic fibers, or natural fibers) may be placed between the plurality of tobacco plugs. The tobacco element 402 may be a "non-combustible" element that may be capable of introducing tobacco flavoring to the heated vapor that may pass through the heater 14, without the element 402 being burned or otherwise combusted.

Mesh screens 406/408 may fit on ends of the housing 404 to enclose the tobacco element 402 within the housing 404. The mesh screens 406/408 may include openings 410 that may allow vapor to pass from one end of the housing 404 through the tobacco element 402 and out of the end of the housing 404 that is closest to the mouth-end insert 8.

The insert 400 may be set closer to the mouth-end insert 8, or closer to the heater 14. The heater 14 may be positioned a distance apart from the tobacco element 402, or alternatively the heater 14 may contact the tobacco element 402, such that the heater 14 may heat the tobacco element 402 to a desired temperature during active operational use of the cartridge 70g while vaping conditions are present in the cartridge 70g (as described above). The heater 14 may warm the tobacco element 402, but the heater 14 is not to burn the tobacco element 402. Thus, the warming of the tobacco element 402 may be referred to as a "non-combustible" process. Because the cartridge 70g may include the tobacco element 402 and the heater 14, the cartridge 70g may therefore be referred to as a "non-combustible smoking element."

Figure 9:
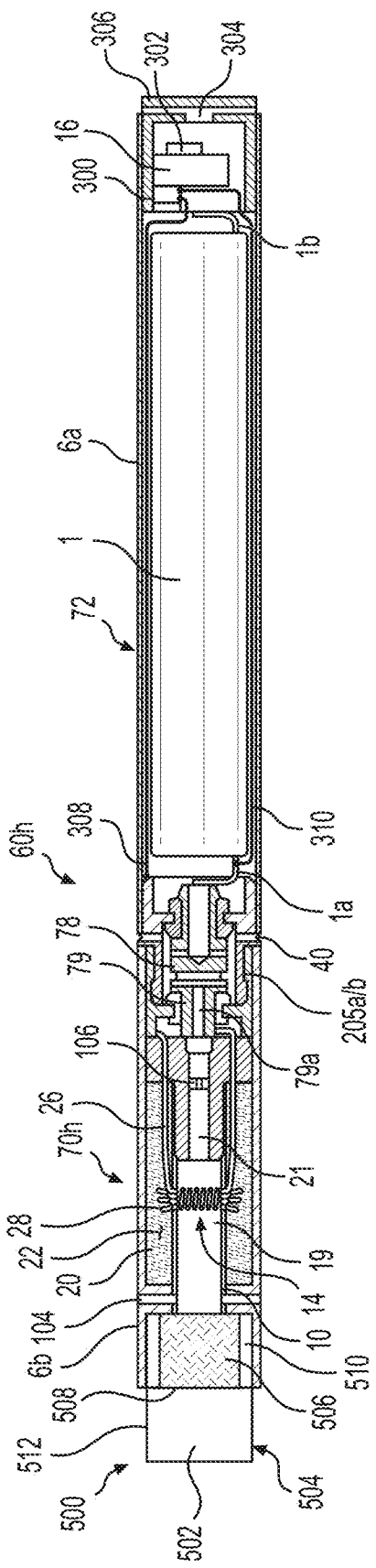
FIG. 9 illustrates an e-vaping device that includes a cartridge with a small diameter gasket and dilution air, with a non-combustible tobacco vaping insert, in accordance with an example embodiment.

FIG. 9 illustrates an e-vaping device 60g that includes a cartridge 70h with a small diameter gasket 106 and dilution air, with an insert 500, in accordance with an example embodiment. The device 60h may be considered another tobacco vapor system, due to the existence of the insert 500. A general size of the cartridge 70h (i.e., overall length, and diameter of the outer air passage 19) may be a same size as the cartridge 70a, described above. The dilution air may be provided by one or more dilution air inlets 104. The location and physical characteristics (i.e., internal diameter) of the gasket 106, and the physical characteristics and location of the dilution air inlets 104, is the same as the cartridge 70c of FIG. 4, and for brevity sake this information is therefore not repeated again, here.

The insert 500 may be fitted on an end of the cartridge 70h, where a filter 502 of the insert 500 may take the place of a typical mouth-end insert (such as the mouth-end insert 8, shown in FIG. 4). In this configuration, the insert 500 may, optionally, include a replaceable tobacco insert 504 within the insert 500, where the tobacco insert 504 may be removed and replaced prior to the useful and-life of the cartridge 70h, following a depletion of a tobacco element 506 within the tobacco insert 504. The tobacco insert 504 may include a tobacco element 506 and a filter 502. The insert 500 may include a housing 510 that may define a receiving area 508 that may hold the replaceable tobacco insert 504.

The tobacco insert 500 may, optionally, be a cigarette or cigar, or a portion of a cigarette or a cigar. As an example, the tobacco insert may be a filtered cigarette, a non-filtered cigarette, a cigarillo, a filter tipped cigar filter, a tipped cigar or an untipped cigar/cigarillo, for example. However, example embodiments are not limited thereto. In an example embodiment, if the tobacco insert 500 is an untipped cigar/cigarillo, the tobacco insert 500 may not include a filter.

Tipping paper 512 may overlap the filter 502 and/or the tobacco element 506. The tipping paper 512 may cover surface areas of the tobacco insert 500 that may extend along an inner surface of housing 6b of cartridge 70h. Thus, the tipping paper 512 may provide stiffness to the tobacco insert 504, permitting easier insertion of the tobacco insert 504 within the receiving area 508. An aluminum foil may also be used to contain the tobacco element 506, and this aluminum foil may either be included in lieu of the tipping paper 512, or in addition to the tipping paper 512. In an embodiment, the filter 502 may be a cellulose acetate (CA) filter.

Example embodiments having thus been described, it should be understood that specific features of the different embodiments (shown in FIGS. 2-9) may be combined, and/or substituted. For example, any of the embodiments involving a flow tube may instead include a gasket in lieu of the flow tube. Similarly, any of the embodiments involving a gasket may instead include a flow tube in lieu of a gasket. Likewise, dilution air may be modified for any of the embodiments, such that bypass vents may be substituted for dilution air inlets, and vice versa. Additionally, non-combustible tobacco vaping inserts may be added, or may be removed, from any of the embodiments described above. Furthermore, other inserts similar to the inserts 400/500, that are with or without tobacco, that may include other materials such as a botanical enclosure, or that may consist simply of a mouth-piece, may be attached to an existing e-vaping device, where the air flow design of the example embodiments may be introduced into the insert and/or the mouth-piece, with minimum retrofit modifications needing to be performed on the existing device. Lastly, the air flow design provided by the example embodiments may be applied to other e-vaping devices, such as devices with a tank-type pre-vapor formulation reservoir, in order to achieve similar results in increasing vapor particle size.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. A method, comprising:
    first establishing a first airflow in a first passage of an e-vaping cartridge, the first passage including a first portion, a second portion and a third portion, a first air inlet in communication with the first portion, a heater in communication with the second portion, the first airflow being defined at least in part by an inner tube and a first seal, the second portion being between the first portion and the third portion;
    second establishing a second airflow in a second passage of the e-vaping cartridge, the first passage being in direct communication with a first outlet of the second passage at the third portion;
    first inserting a first airflow restrictor in the first airflow within the first passage at a first location that is upstream of the first outlet relative to a normal direction of the first airflow through the e-vaping cartridge, the first airflow restrictor being within the first seal or the inner tube; and
    second inserting a pressure drop element between a second outlet of the first passage and the first outlet, the pressure drop element being at least one of a tobacco element or a second airflow restrictor.

2. The method of claim 1, wherein the first airflow restrictor is at least one of a flow tube or a gasket.

3. The method of claim 1, further comprising:
    communicating a pre-vapor formulation from a reservoir to the heater; and
    entraining the first airflow with a vapor by at least partially vaporizing the pre-vapor formulation using the heater.

4. The method of claim 1, wherein the second establishing establishes the second airflow to be combined with the first airflow prior to flowing through a fourth portion of the first passage and exiting the e-vaping cartridge through a mouth-end insert, the mouth-end insert defining the second outlet.

5. The method of claim 1, wherein the second establishing establishes the second airflow to draw ambient air directly into the third portion, a second air inlet of the e-vaping cartridge forming an entrance for the second passage.

6. The method of claim 1, wherein the second establishing establishes the second airflow to bypass the heater, an entrance of the second passage being in direct communication with at least one of the first portion or the second portion.

7. The method of claim 4, wherein the second inserting inserts the second airflow restrictor within the fourth portion, the second airflow restrictor being a second seal, a first internal diameter of the second seal being smaller than a second internal diameter of the fourth portion.

8. The method of claim 4, wherein the second inserting inserts the tobacco element in the fourth portion, the tobacco element being contained in an insert that is selectively connectable to the second outlet.

9. The method of claim 1, wherein the first establishing establishes the first airflow at least in part by further defining the first passage via a housing of the e-vaping cartridge, or an electrical terminal on a first end of the e-vaping cartridge, the first seal being near the first end.

10. The method of claim 2, wherein the first inserting inserts the first airflow restrictor in the first passage between the heater and the first air inlet.

11. The method of claim 2, wherein the first inserting inserts the first airflow restrictor that has a first cross-sectional flow area that is 5-25% as large as a second cross-sectional flow area of the second portion, the first airflow restrictor being in the second portion.

12. The method of claim 2, wherein the first inserting inserts the flow tube in the second portion, the flow tube having a first internal diameter between 0.8 mm and 2 mm, and a second internal diameter of the second portion being in a range of 2 mm to 6 mm.

13. The method of claim 12, wherein the flow tube has a length between about 8 mm and 12 mm.

14. The method of claim 2, wherein the first inserting inserts the gasket in the second portion, the gasket having a third internal diameter between 0.6 mm and 1.0 mm, a second internal diameter of the second portion being in a range of 2 mm to 6 mm.

15. The method of claim 14, wherein the gasket has a length of 1 mm.

16. The method of claim 1, further comprising:
connecting the e-vaping cartridge to a power section to form an e-vaping device, the power section including a power source electrically and operationally connected to the heater when the e-vaping cartridge is connected to the power section.

17. The method of claim 16, wherein the first establishing establishes the first airflow at least in part by defining the first air inlet via a first housing of the e-vaping cartridge, a second housing of the power section or both the first housing and the second housing.

18. The method of claim 16, wherein the first establishing establishes the first airflow by defining a third air inlet via a first housing of the e-vaping cartridge, a second housing of the power section or both the first housing and the second housing, the third air inlet being in communication with the first air inlet.

* * * * *